(12) United States Patent
Romero et al.

(10) Patent No.: US 9,139,858 B2
(45) Date of Patent: *Sep. 22, 2015

(54) METHOD AND APPARATUS FOR MIXING A LIGNOCELLULOSIC MATERIAL WITH ENZYMES

(71) Applicant: Andritz Inc., Glens Falls, NY (US)

(72) Inventors: Rodolfo Romero, Clifton Park, NY (US); Bertil Stromberg, Diamond Point, NY (US)

(73) Assignee: Andritz Inc., Glens Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/101,996

(22) Filed: Dec. 10, 2013

(65) Prior Publication Data

US 2014/0113334 A1   Apr. 24, 2014

Related U.S. Application Data

(62) Division of application No. 13/301,007, filed on Nov. 21, 2011, now Pat. No. 8,617,355.

(60) Provisional application No. 61/415,849, filed on Nov. 21, 2010, provisional application No. 61/415,847, filed on Nov. 21, 2010.

(51) Int. Cl.
*C12P 19/00* (2006.01)
*C13K 1/02* (2006.01)
(Continued)

(52) U.S. Cl.
CPC ............... *C12P 19/14* (2013.01); *C12M 21/18* (2013.01); *C12M 45/02* (2013.01); *C12M 45/09* (2013.01); *C12M 45/20* (2013.01); *C12P 19/02* (2013.01)

(58) Field of Classification Search
USPC ............ 435/72, 158, 289.1, 294.1; 162/9, 21, 162/52, 57, 233, 243, 261; 127/37
See application file for complete search history.

(56) References Cited

U.S. PATENT DOCUMENTS

| 8,389,243 | B2 | 3/2013 | Gao et al. |
| 2009/0053777 | A1 | 2/2009 | Hennessey et al. |

(Continued)

FOREIGN PATENT DOCUMENTS

| WO | 2005/118828 A1 | 12/2005 |
| WO | 2009/045651 A2 | 4/2009 |
| WO | 2009/046524 A1 | 4/2009 |
| WO | 2011/080154 A1 | 7/2011 |

OTHER PUBLICATIONS

Roche et al., "Laboratory-scale method for enzymatic saccharification of lignocellulosic biomass at high-solids loadings", Biotechnolgy for Biofuels, Nov. 4, 2009, p. 28, vol. 2, No. 1, Biomed Central LTD, London, UK.

(Continued)

*Primary Examiner* — Dennis Cordray
(74) *Attorney, Agent, or Firm* — Kerri Hochgesang; Robert Joseph Hornung (57) ABSTRACT

A method to treat a lignocellulosic material including: pretreating the lignocellulosic material to produce a slurry; adding an alkali material to the slurry in a first conveyor; adding a first portion of an enzyme solution to the slurry while the slurry is in, entering or passing through the discharge of a second conveyor; transferring the slurry with the enzyme solution from the second conveyor slurry to a mixer; mixing the slurry with a second portion of the enzyme solution, and transferring the slurry with the enzyme solution mixed with the first and second portions of the enzyme solution to a first reactor vessel for enzymatic hydrolysis, wherein the viscosity of the slurry is reduced in the first reactor vessel.

22 Claims, 7 Drawing Sheets

(51) Int. Cl.
  *D21B 1/36* (2006.01)
  *D21C 1/00* (2006.01)
  *C12P 19/14* (2006.01)
  *C12M 1/40* (2006.01)
  *C12M 1/00* (2006.01)
  *C12P 19/02* (2006.01)
  *C12M 1/33* (2006.01)

(56) References Cited

U.S. PATENT DOCUMENTS

2009/0098616 A1   4/2009   Burke et al.
2010/0317053 A1   12/2010  Stromberg et al.

OTHER PUBLICATIONS

Jorgensen et al., "Liquefaction of ligno-cellulose at high-solids concentrations", Biotechnology and Bioengineering, Apr. 1, 2007, pp. 862-870, vol. 96, No. 5, Wiley & Sons, Hoboken, NJ, US.

Kristensen et al., "Yield-determining factors in high-solids enzymatic hydrolysis of lignocellulose", Biotechnology for Biofuels, Jun. 8, 2009, pp. 1-10, vol. 2, No. 11, Biomed Central LTD, London, UK.

Lu et al., "Influence of high solid concentration on enzymatic hydrolysis and fermentation of steam-exploded corn stover biomass", Applied Biochemistry and Biotechnology, Jan. 1, 2010, pp. 360-369, vol. 160, No. 2, Humana Press, Inc., United States.

Georgieva et al., "Enxymatic hydrolysis and ethanol fermentation of high dry matter wet-exploded wheat straw at low enzyme loading", Applied Biochemistry and Biotechnology, Mar. 2008, pp. 35-44, vol. 148, Nos. 1-3, US LNKD.

Rosgaard et al., "Effects of substrate loading on enzymatic hydrolysis and viscosity of pretreated barley straw", Applied Biochemistry and Biotechnology, Oct. 2007, pp. 27-40, vol. 143, No. 1, US LNKD.

Pamlqvist et al., "Effect of mixing on enzymatic hydrolysis of steam-pretreated spruce: a quantitative analysis of conversion and power consumption", Biotechnology for Biofuels (online), May 11, 2011, pp. 1-8, vol. 4, No. 10.

International Search Report for PCT Application No. PCT/US2011/061670 (Feb. 17, 2012).

METHOD AND APPARATUS FOR MIXING A LIGNOCELLULOSIC MATERIAL WITH ENZYMES

CROSS RELATED APPLICATIONS

This application is a divisional of U.S. application Ser. No. 13/301,007, filed Nov. 21, 2011, and claims the benefit of U.S. patent application Ser. Nos. 61/415,849, and 61/415,847, filed on Nov. 21, 2010, all of which applications are incorporated by reference in their entirety.

BACKGROUND OF THE INVENTION

This invention relates generally to the field of enzymatic conversion of lignocellulosic material to monomeric sugars and particularly to maximizing enzyme performance during a liquefaction stage of pretreated lignocellulosic material.

Enzymatic hydrolysis of pretreated lignocellulosic material poses many challenges. These challenges go from the interaction of the enzymes themselves with the biochemical complexity of the pretreated material and its derivatives and to the physical characteristics of the liquid/fiber, monomeric/oligomeric mixture (collectively referred to as a "slurry") and its rheological features.

A conventional reactor to accomplish enzymatic hydrolysis required large batch tanks having expensive and powerful impellers to mix the enzymes into the slurry. Enzymatic liquefaction of lignocellulosic material may require several hours of mixing in the large batch tanks. The mixing process reduces the viscosity of the lignocellulosic material by converting the material from a generally solids composition to a liquefied slurry. The pretreated lignocellulosic material typically starts the mixing and process having a mud-like consistency.

Lignocellulosic material is pretreated and subjected to enzymatic conversion to monomeric sugars. The enzymes added to the lignocellulosic material typically have a relatively low concentration with respect to the lignocellulosic material. The lignocellulosic material and enzyme mixture tends to be highly viscous as it enters a mixing and pretreatment reactor system. The high viscosity of the mixture has motivated the use of relatively small reactor vessels to reduce the torque needed to mix the mixture. Such a system typically includes one or more hydrolysis reactor vessels.

The mixing vessels of a conventional mixing and pretreatment reactor system for enzymatic liquefaction of lignocellulosic material have traditionally been operated in a batch mode rather than a continuous mode. A batch mode for mixing is often better suited to situations were several smaller mixing vessels feed a larger downstream vessel, such as a digester or other reactor vessel.

Recirculation of liquefied material to dilute the incoming pretreated lignocellulosic material has been proposed to decrease the viscosity, and improve the mixing. Recirculation has a disadvantage in that additional mixing volume is required to achieve the desired retention time in the vessel. Batch processing adds volume to the system, as time has to be provided to fill and empty the vessel.

SUMMARY OF THE INVENTION

There is a long felt need for large mixing vessels capable of mixing highly viscous lignocellulosic material with enzymes. These vessels may be continuous flow vessels in which lignocellulosic material flows continuously in, through and out of the vessel. A large vessel would provide efficient, high flow capacity for mixing lignocellulosic material and enzymes.

The invention may involve the addition of one or more enzymes, optionally in a solution, to a viscous slurry to quickly reduce the viscosity of the slurry. The reduction in viscosity may result in the slurry having characteristics more similar to a liquid than to a solid or thick mud like consistency. For example, the addition of enzymes to a lignocellulosic material causes an enzymatic hydrolysis reaction which reduces the viscosity of the material to the consistency akin to a liquid and yields monomeric sugar(s).

A system has been conceived to liquefy a lignocellulosic material comprising: a steam explosion reactor receiving the lignocellulosic material saturated with water, subjecting the material to a rapid pressure release to cause a steam explosion reaction and discharging a slurry comprising the lignocellulosic material after the steam explosion reaction; a first screw conveyor in fluid communication with a discharge of the steam explosion reactor, the first screw conveyor including a rotating screw through which passes the slurry discharged from the steam explosion reactor, and an inlet through which an alkali-based material is injected into the slurry passing through the first screw conveyor; a second screw conveyor in fluid communication with a discharge of the slurry from the first screw conveyor, wherein the second screw conveyor includes a rotating screw through which passes the slurry from the first screw conveyor and a plurality of inlets for an enzyme to be injected into the slurry in the second screw conveyer; a mixer in fluid communication with a discharge of the second screw conveyor, wherein the mixer includes a mixing device rotating at a speed of about 400 to 4,000 rpm, and the mixer retains the slurry from the second screw conveyor for about 0.05 to 200 seconds, and the mixing includes an inlet through which the enzyme solution is added to the slurry during mixing; a first reactor to transition the material from a higher viscosity to a lower viscosity to create a substantially liquid material, wherein the first reactor includes inverted conical upper section having a mixing device with rotating radial arms which are progressively longer in a downward direction through the upper section.

The method has been conceived comprising: performing a steam explosion reaction to produce a slurry comprising lignocellulosic material; mixing the slurry with alkali-based materials and water in a first conveyor until an average pH of the slurry is from about 4.5 to 6.5 , an average temperature of the slurry is from about 45 to 55 degrees Celsius (C), and the slurry has a consistency (wt % of weight of insoluble particles as compared to total weight of the slurry) of from about 10 to 35%; transferring the slurry to a second conveyor; adding a first portion of an enzyme solution to the slurry in the second conveyer, wherein the enzyme is added to the conveyer from more than one location inside the second conveyor; transferring the slurry to a mixer via a positive displacement pump; mixing the slurry in a mixer at a speed of from about 400 to 4,000 rpm, for about 0.05 to 200 seconds, wherein a second portion of the enzyme solution is added to the slurry during said mixing; transferring the slurry to a first reactor to transition the material from a higher viscosity to a lower viscosity to create a substantially liquid material, wherein the first reactor is an inverted conical vessel; and transferring the substantially liquid material to a second reactor for further liquefaction and enzymatic hydrolysis, wherein the temperature of the slurry is kept at a temperature of from about 45 to 55 degrees from just prior to the addition of the first portion of the enzyme solution and throughout the duration of the process.

DETAILED DESCRIPTION OF THE INVENTION

The invention disclosed herein may be used in a process to derive, produce or extract simple compounds from wood, pulp, fiber, and the like, for use in other applications such as the production of fuel, including ethanol gas. In other embodiments, the invention may be applied to decrease the viscosity of viscous, cellulose-containing material to facilitate transport of the material for other processes. Further, the invention may be embodied to extract monomers of certain compounds from cellulose-containing materials, such as lignocellulosic materials. In addition, the invention may be applied to enzymatically hydrolyze pretreated lignocellulosic materials in order to produce monomeric sugars.

Enzymatic hydrolysis on lignocellulosic materials is challenging, especially with respect to the interactions between the enzymes and the lignocellulosic materials (and its derivatives), and due to the physical characteristics of the fibers, the monomeric/oligomeric mixture, e.g., slurry, and the rheological features thereof of the lignocellulosic material.

There is a long felt need to increase the enzyme performance during the liquefaction stage of pretreated lignocellulosic material, and particularly to increase the enzyme performance in a timely fashion to positively impact the efficiency of the process of liquefaction, such as accelerating the liquefaction process. Enzymes are a type of catalysts, and in certain cases, enzymes work by lowering the activation energy for a reaction, thus increasing the rate at which the reaction will occur. As a result, products may be formed faster through the use of enzymes.

Particular enzymes may only work for specific "substrates" or reactants. In certain example embodiments, the enzymes used to catalyze the liquefaction of the lignocellulosic materials may comprise cellulases or xylanases.

In certain instances, cellulases are enzymes that catalyze cellulolysis, e.g., the hydrolysis of cellulose. There are several general types of cellulases. The appropriate cellulases to be used as an enzyme depends on the reaction to be catalyzed. One example is endo-cellulase, which breaks internal bonds to disrupt the crystalline structure of cellulose and expose individual cellulose polysaccharide chains. Another example is exo-cellulase, which cleaves 2-4, units from the ends of the exposed chains produced by endocellulase, resulting in the tetrasaccharides or disaccharide such as cellobiose. In certain example embodiments, there are two primary types of exo-cellulases (or cellobiohydrolases, abbreviate CBH)—one type works progressively from the reducing end, and one type works progressively from the non-reducing end of cellulose. Another non-limiting example of a cellulase is cellobiase or beta-glucosidase, which hydrolyses the exo-cellulase product into individual monosaccharides. A still-further non-limiting example of cellulases includes oxidative cellulases, which depolymerize cellulose by radical reactions. An additional example of cellulases is cellulose phosphorylases, which depolymerize cellulose using phosphates instead of water. This list of celluloses is for illustrative purposes only, and is not meant to be limiting. In certain example embodiments, any cellulase-based enzyme may be used.

In other example embodiments, xylanase may be used in addition to or instead of a cellulase. In certain instances, xylanase may refer to a class of enzymes which degrade the linear polysaccharide beta-1,4-xylan into xylose, a monomeric sugar (e.g., a monosaccharide). In certain example instances, xylanase may assist with breaking down hemicellulose. However, this is non-limiting and in certain example embodiments any xylanase-based enzyme may be used for any applicable purpose or reaction.

In certain example embodiments, particular enzymes may only work for specific "substrates" or reactants. Moreover, in certain cases, some enzymes work better in specific conditions. In certain example embodiments, some enzymes may function better (e.g., permit the overall reaction to occur faster or to a further extent) in a particular temperature range, a particular pH range, or at particular concentration of reactants.

In certain example embodiments, particularly when a cellulase or xylanase-based enzyme is added to a slurry comprising a mixture of lignocellulosic material (and optionally water), the temperature of the mixture, and the temperature at which the reaction is occurring is controlled to be in ranges such as 40 and 60 degrees Celsius (C), 45 to 55 degrees C., and 48 to 50 degrees C. In other example embodiments, the pH of the mixture may be controlled throughout the reaction, e.g., the liquefaction process to be ranges such as about 4 to 6, about 4.5 to 5.5, and 5 to 6 . In certain examples, these temperature and pH ranges may be particularly advantageous in that the enzyme functions "better" (e.g., the reaction/process may proceeds faster or to a more complete extent).

In certain example embodiments, the slurry comprising pre-treated lignocellulosic material may result from a steam explosion-type process. In an example embodiment of such a process shown in FIG. 1, wood chips may be impregnated with warm or hot (e.g., above room temperature), under high pressure, such that the water gets into the cell structure of the wood chips. These impregnated materials 9 under high pressure will then be transferred to a cyclone or some type of container which is at a lower pressure (e.g., substantially atmospheric pressure). In certain example embodiments, such a transition from high pressure to low pressure may result in vaporization of some of the water. The cyclone 10 containing the materials from the steam explosion may have vents to release the vapor.

Figure 1:
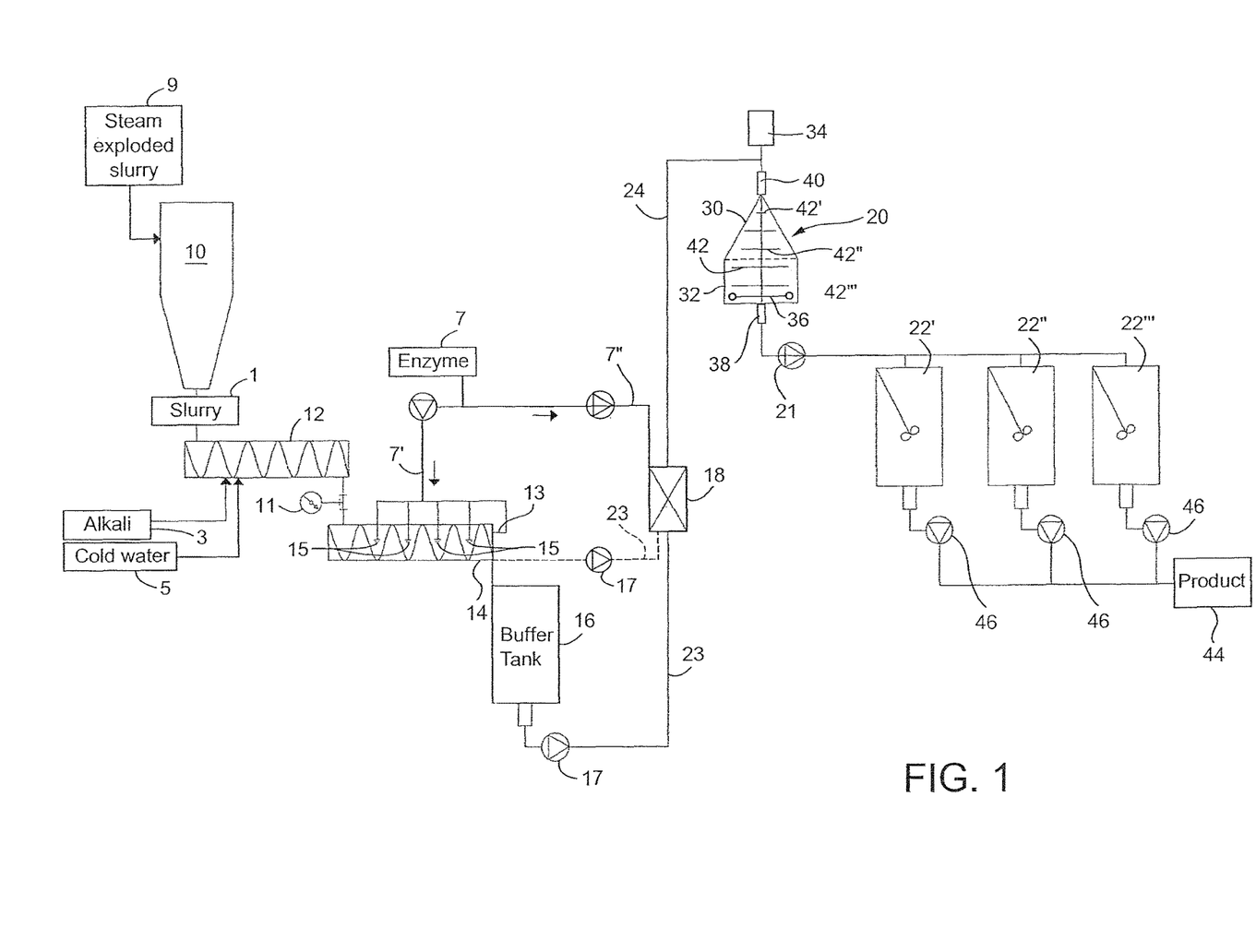
FIG. 1 is a process flow diagram of the overall process by which the lignocellulosic materials are mixed with one or more enzymes or enzyme-containing solutions in an enzymatic hydrolysis reaction in order to produce monomeric sugars or other useful by-products.

In certain example embodiments, after lignocellulosic materials have been subject to a steam explosion process, or other pre-treatment methods, the resulting slurry is transferred to a cyclone 10. The resulting slurry of lignocellulosic materials will be at an elevated temperature—up to about 300 degrees C., or a range of 75 to 200 degrees C., and 100 to 200 degrees C. In cyclone 10, the materials may remain at substantially atmospheric pressure in certain example embodiments.

In certain instances, the consistency (the percent by weight of insoluble solid particles in the mixture comprising those particles and water) of the slurry is from about 20 to 50% (wt %). In further example embodiments, the pH of the slurry may be from about 1 to 4 (and all sub-ranges therein). In certain example embodiments, the pH of the slurry may need to be raised in order for the conditions to be more ideal for the enzyme. In further example embodiments, the temperature of the slurry may need to be lowered in order for it to be within the temperature range that is more ideal for the enzyme's performance.

FIG. 1 shows an exemplary embodiment for mixing an enzyme with lignocellulosic material-based slurry 9. In certain example embodiments, after this steam explosion or other pre-treatment process, the slurry 9 comprising the lignocellulosic materials is transferred from a cyclone 10 or whichever vessel type in which the pre-treatment was performed to a first conveyor 12. The slurry 9 in the cyclone may be at a temperature of about 100 degrees C. (within 15 degrees of 100 C.), be 40% solids by weight and have a pH of 1 to 4. From the cyclone, the slurry 1 is transferred to the conveyor 12. The first conveyor 12 may be a screw, or more particularly, a "cooling and pH adjustment screw." In this conveyor 12, in certain examples, the temperature or pH of the slurry may be altered, as described above, such that the conditions are made more ideal for the enzyme. In certain example embodiments, the temperature of the slurry is lowered, and the pH is raised. However, this is illustrative only, and may not always be the case depending on the pH or temperature of the mixture during or after pre-treatment.

In certain example embodiments, while in the conveyor 12, pH-changing materials 3, such as an alkali material, or temperature-changing materials 5, such as cold water, may be added to the slurry in order alter the pH, or consistency or temperature of the slurry such that these values fall into the ranges as described above. A sensor 11, such as a temperature sensor, may monitor the slurry discharged by the conveyor 12 and provide data for adjusting the pH and temperature of the slurry in the conveyor 12. In certain examples, the pH-changing materials 3 may be alkali-based compounds or the temperature-changing materials 5 may be cold water e.g., water at a temperature lower than the initial temperature of the slurry. In other example embodiments, if the temperature of the slurry is too high, or the pH is too high, pH and temperature-changing materials comprising acidic compounds or warm water may be added in order to alter the pH or temperature of the slurry such that these values fall into the above-described ranges. In further example embodiments, while in the first conveyor, the consistency of the slurry is reduced to about 10 to 30% by weight, or to about 15 to 30%, or to about 18 to 25%.

After the pH, temperature, or the consistency of the slurry is altered via the addition of pH-changing materials 3 e.g., alkali compounds, and temperature changing materials 5, e.g., cold water, in first conveyor 12 so as to fall within a more ideal or desired range for performance of the enzyme, the slurry 1 may be transferred to a second conveyor 14 which may also be a screw conveyor. In this second conveyor, a portion 7' of the enzyme solution 7 may be sprayed or otherwise combined with the slurry in the conveyor 14. In some cases, the enzyme solution 7' may be sprayed in the conveyor via spray nozzles 15 that are evenly distributed throughout the conveyor. For example, the inlets for enzyme injection may be equally spaced at a plurality of locations along a longitudinal length of a screw of the second screw conveyor. In other example embodiments, the enzyme solution 7' may be added to the slurry via axial inlets 13 (which may be on both ends of the conveyor) not shown in FIG. 1, or inlets located in various irregularly spaced positions on the conveyor 14 (also not shown in FIG. 1).

Following the addition of the enzyme solution portion 7' to the slurry, the slurry (including the enzyme solution 7') may be transferred to a vessel 16. In certain example embodiments, the slurry will remain in vessel 16 until more slurry added to the vessel for the remaining processing steps. The vessel 16 may be a buffer tank. In other example embodiments, the slurry may be transferred directly to a mixer 18, rather than going to the vessel 16. In some instances, a positive displacement pump 17 may be used to transfer the slurry to the mixer 18 via pipes 23. The positive displacement pump 17 may be a medium consistency positive displacement pump. The positive displacement pump may alternatively be in a pipe extending directly from the conveyor 14 to the mixer 18.

In certain example embodiments, when the slurry is transferred to the mixer 18, the slurry has a viscosity of greater than about 15,000 mPa·s, more particularly a viscosity of greater than about 20,000 mPa·s, and in certain examples, it may even have a viscosity of greater than about 25,000 mPa·s.

The mixer 18 may be a medium consistency (MC) mixer. The enzyme solution portion 7" may be added to mixer 18 with the slurry. Alternatively, once the slurry is transferred to mixer 18, the slurry may be mixed, and thereafter portion 7" of the enzyme solution 7 may be added to the slurry. In some cases, the enzyme solution 7" may be added prior to mixing the slurry and enzyme solution portion. In other example embodiments, the solution 7" may be added simultaneously to, or subsequent to, the start of the mixing. In further example embodiments, solution 7" may be added to the mixer 18 at the same time that the slurry is added to mixer 18 such that both the slurry and enzyme solution portion 7" are both present prior to the start of mixing.

In an exemplary embodiment, the enzyme solution portion 7" and the slurry are added to the mixer 18 substantially simultaneously, while the mixer is operating at rotational speeds such as speeds in ranges of 200 to 6,000 rpm (revolutions per minute), 300 to 5,000 rpm, and 400 to 4,000 rpm. The slurry and the enzyme portion 7" may be mixed for certain predetermined periods such as periods in ranges of 0.05 to 500 seconds, 0.1 to 300 seconds, and 0.1 to 100 seconds. Mixing of the slurry and enzyme solution portion 7" in the mixer 18 in this manner and at the above-discussed speeds may advantageously result in a faster digestion of the fibers in the slurry, without significantly degrading or denaturing the enzymes from the enzyme solution.

After both enzyme portions 7' and 7" have been mixed into the slurry, the slurry is them transferred e.g., pumped, to another vessel 20. The vessel 20 may be a high consistency reactor or mixer. The vessel 20 may permit a smoother transition from a very viscous material to a less viscous material, or even a liquid, in certain example embodiments.

Figure 2:
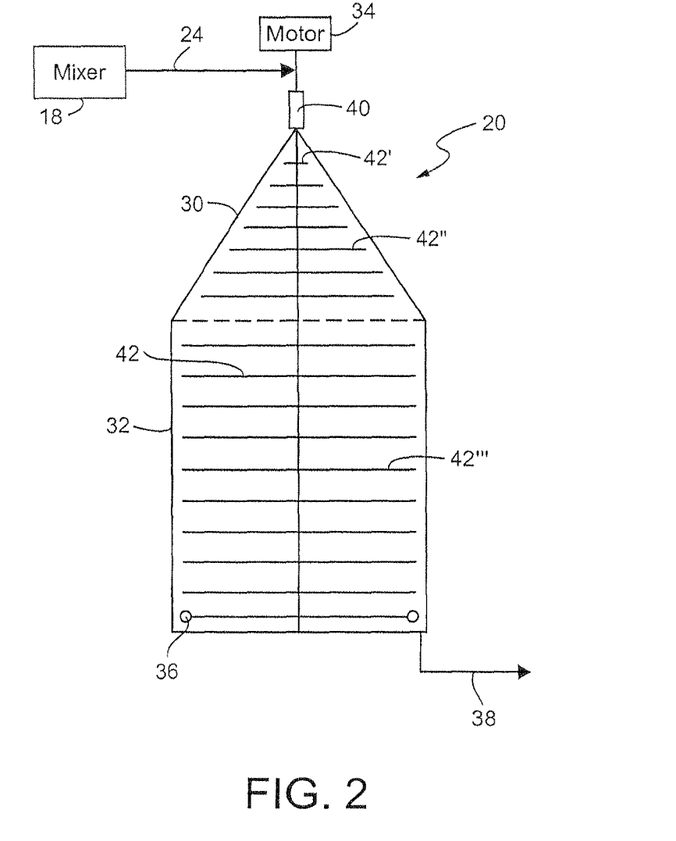
FIG. 2 is a schematic diagram of a reactor having an upper inverted conical portion and an optional lower cylindrical portion.

FIG. 2 shows an example exemplary embodiment of vessel 20. In certain exemplary embodiments, the vessel 20 may comprise a reactor and mixing vessel having a conical upper section 30 and a cylindrical lower section 32. These sections 30, 32 define an internal reaction chamber in which the slurry is further mixed with the enzyme(s) and is at least partially hydrolyzed. The internal reaction chamber of vessel 20 may have a volume of 20,000 cubic meters; 25,000 cubic meters or more (or less). The reaction chamber may be substantially larger in volume than conventional batch mixing/reactor vessels conventionally used to mix highly viscous slurry.

The vessel includes a rotatable shaft 36 extending along the vertical axis of the vessel. The shaft is driven (rotated) by a motor and gear box assembly 34, which may be mount to the top or bottom of the vessel. The shaft 36 is coaxial to a vertical axis of the vessel and extends along the height of the vessel.

The pre-treated slurry 24 comprising lignocellulosic materials, enzymes and possibly other components may be continuously fed to an upper inlet 40 of the vessel 20. The slurry (including the enzymes) may be fed as a mixture to the vessel. In other embodiments, the slurry and further portions of enzymes or enzyme solutions may be fed separately to the vessel 20. If desired, recycled low viscosity hydrolyzed slurry could also be introduced into the upper inlet 40 of the vessel 20.

The inlet 40 feeds the slurry to a narrow region of the conical upper section 30. The bottom of the lower section is adjacent a discharge outlet 38 for the partially or substantially hydrolyzed slurry continuously flowing out of the vessel 20 via pump 21 to other process units, such as another reactor.

In certain instances, the slurry may initially be a viscosity of greater than about 12,500 mPa·s (milli Pascal per second), more particularly greater than about 15,000 mPa·s, and even greater than about 20,000 mPa·s, when the slurry first arrives in vessel 20. In certain example embodiments, the viscosity of the slurry may change from the aforesaid highly viscous values to less viscous values such as less than about 5,000 mPa·s, less than about 3,000 mPa·s, and less than about 2,000 mPa·s. In certain example embodiments, the slurry may even become a liquid.

The conical upper section 30 of vessel 20 is narrow at the inlet 40 that receives the highly viscous slurry entering the vessel. While the high viscosity of the slurry increases the starting torque needed to turn the mixing device, the torque is lessened because of the short mixing arms 42' at the narrow top. The slurry may become less viscous as it moves down through the vessel. The lessening viscosity reduces the demand for torque to turn the mixing arms, in certain example embodiments. The arms in the lower portions of the upper conical section 42'' are longer than the upper arms 42'. Longer arms require more torque to be turned through the slurry. The combined effects of the reduction in viscosity of the slurry and the longer arms results in acceptable torque requirements for the mixing device in the upper conical section. As well as allowing for a relatively large capacity vessel 20.

The lower cylindrical portion 32 of the vessel 20 may have mixing arms and leg 42 and 42''' of uniform length. A discharge device 36 at the bottom of the vessel moves material discharged from the vessel. In certain example embodiments, the process of reducing the viscosity of the slurry in vessel 20 may require certain predetermined periods in a ranges of about 5 to 2000 minutes (min.), of about 10 to 1000 min., and of about 10 to 600 min. (and all subranges therebetween).

As shown in FIG. 1, after the slurry has become a liquid in vessel 20, a pump 21 may be used to transfer the liquid to another reactor 22 where further liquefaction or further enzymatic hydrolysis may take place, in certain example embodiments. Pump 21 used to transfer the liquid to reactor 22', 22'' 22''' may be a centrifugal or positive displacement pump in certain example embodiments. In further example embodiments, reactor 22 may be an enzymatic hydrolysis reactor. In some cases, substantially complete enzymatic hydrolysis may take place in one or more reactors 22', 22'', 22''', each with rotating mixing devices. The product 44 discharged from the reactors 22', 22'', 22''' may be a liquefied slurry of the cellulosic material after enzymatic hydrolysis.

In certain example embodiments, products 44 of the enzymatic hydrolysis process may include sugars, such as monomeric sugars. These products may be pumped by positive displacement pumps 46 to be used in a wide variety of fields or uses. The products 44 may be used to produce ethanol, or any other value-added chemical.

While a continuous flow system has been described herein as an example of an embodiment of the invention, another embodiment in a batch system in which the batches of cellulosic material are mixed in the manner described above mixing could reduce the amount of total enzyme needed for liquefaction or saccharification than otherwise would be higher as in conventional batch or fed-batch system. A batch process could be implemented with or without the inverted tank.

Though the temperature or pH of the slurry may fluctuate slightly throughout the hydrolysis process, it is advantageous for the temperature to remain under about 50 degrees C., and the pH to remain in the range of about 5 to 6,in order to increase the enzyme performance, in certain example embodiments.

Figure 3:
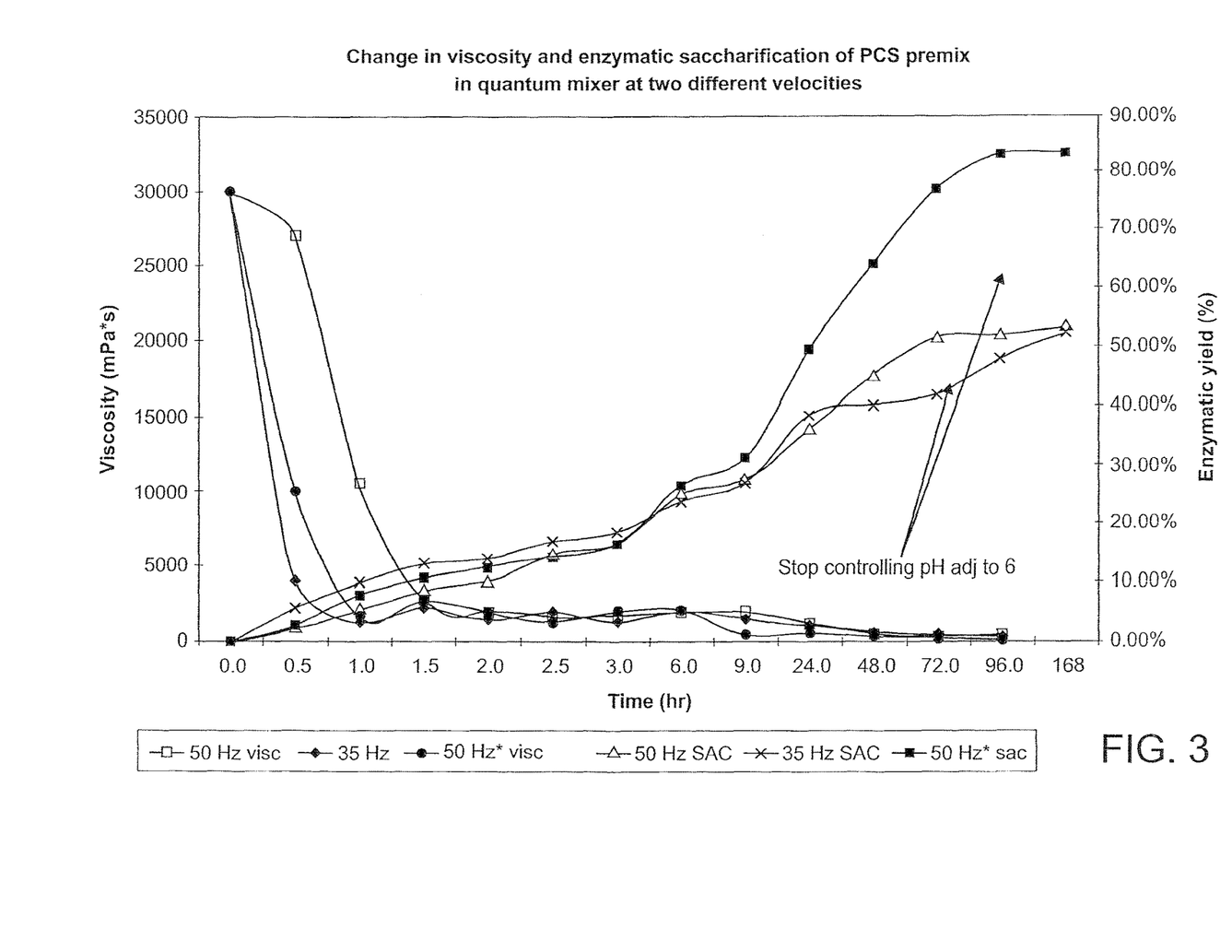
FIG. 3 is a graph illustrating the change in viscosity of the slurry during saccharification and change in enzymatic yield during liquefaction

FIG. 3 is a graph illustrating the change in viscosity and enzymatic saccharification of a PCS premix in a quantum mixture at two different velocities. The data in FIG. 3 indicates that the viscosity of a cellulosic containing slurry falls quickly during enzymatic saccharification and the enzymatic yield rises relatively slowly as compared to the fall in viscosity. FIG. 3 supports the use of an inverted conical first reactor to mix a cellulosic material and enzyme during a relatively short period, e.g., 0.5 hour to 1.5 hours, while the viscosity of the material is high. The inverted conical first reactor is suited to mixing a material having a rapidly reducing viscosity because the upper region of the conical first reactor has relatively short mixing arms adapted to mix a highly viscous material and the arms progressively lengthen in a downward direction of the vessel which corresponds to the reducing viscosity of the material.

Figure 4:
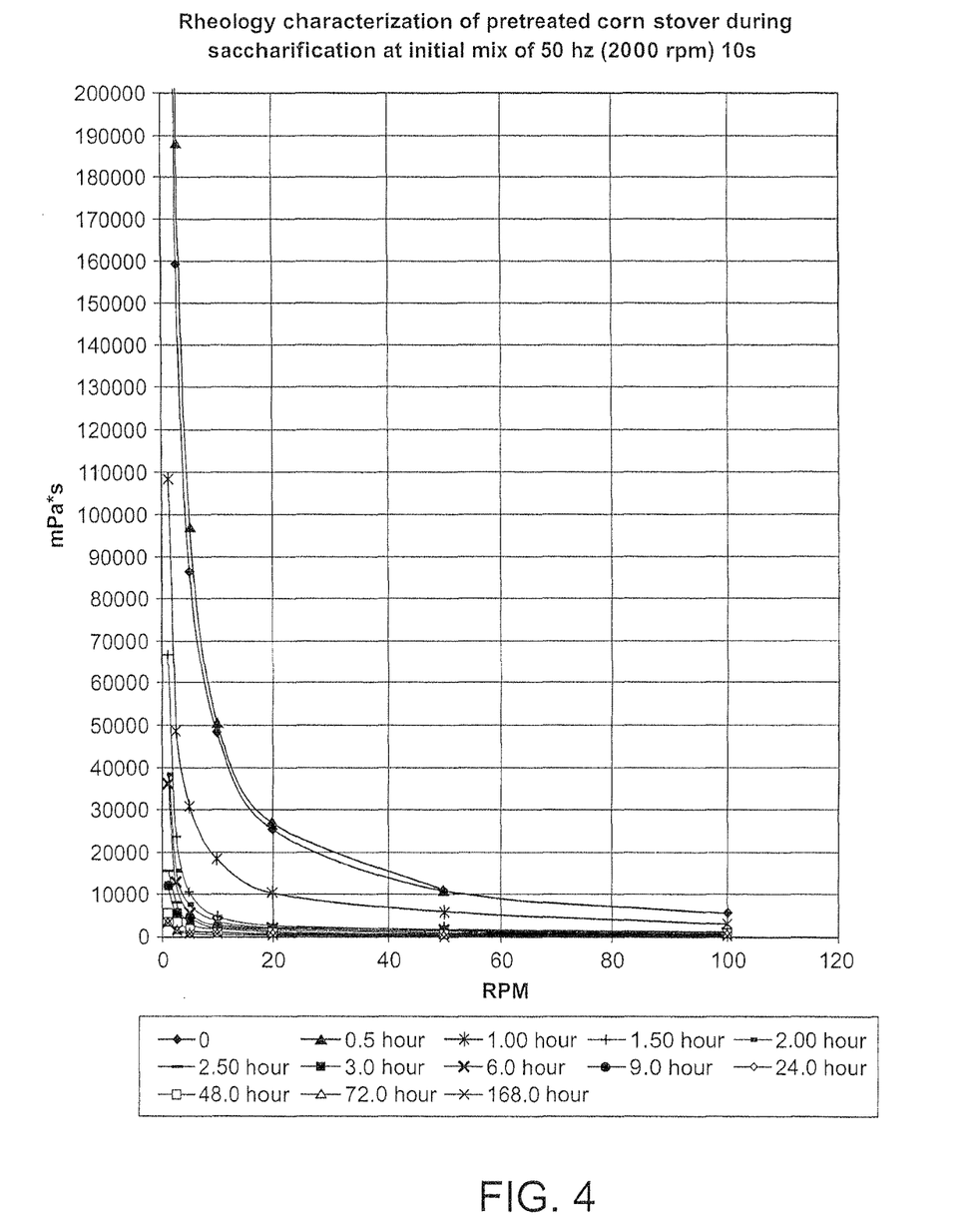
FIG. 4 is a graph illustrating rheology characterization during saccharification.

FIG. 4 is a graph illustrating the rheology characterization of pretreated corn stover during saccharification at an initial mix of 50 hz (2000 rpm) and 10 seconds. FIG. 4 shows that the viscosity (mPa*s) of corn stover is reduced by mixing the stover during enzymatic saccharification at rotational speeds of above 20 rpm, and after the initial mix of enzymatic saccharification.

Figure 5:
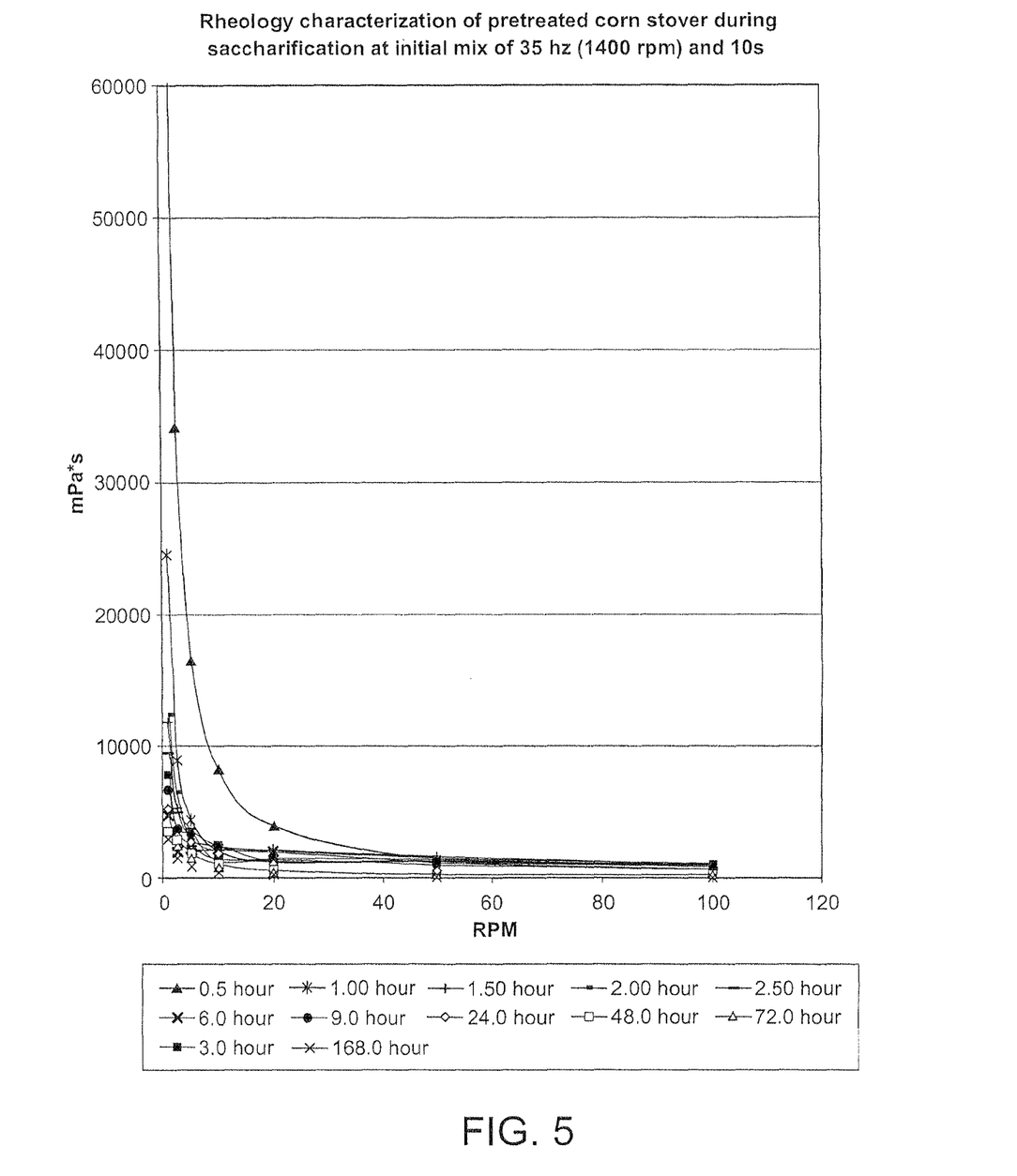
FIG. 5 is a graph also illustrating rheology characterization during saccharification.

FIG. 5 is a graph illustrating the rheology characterization of pretreated corn stover during saccharification at an initial mix of 35 hz (1400 rpm) and 10 seconds. FIG. 5 shows that the viscosity (mPa*s) of corn stover is reduced by mixing the stover during enzymatic saccharification at rotational speeds of above 20 rpm, and after the initial mix of enzymatic saccharification.

Figure 6:
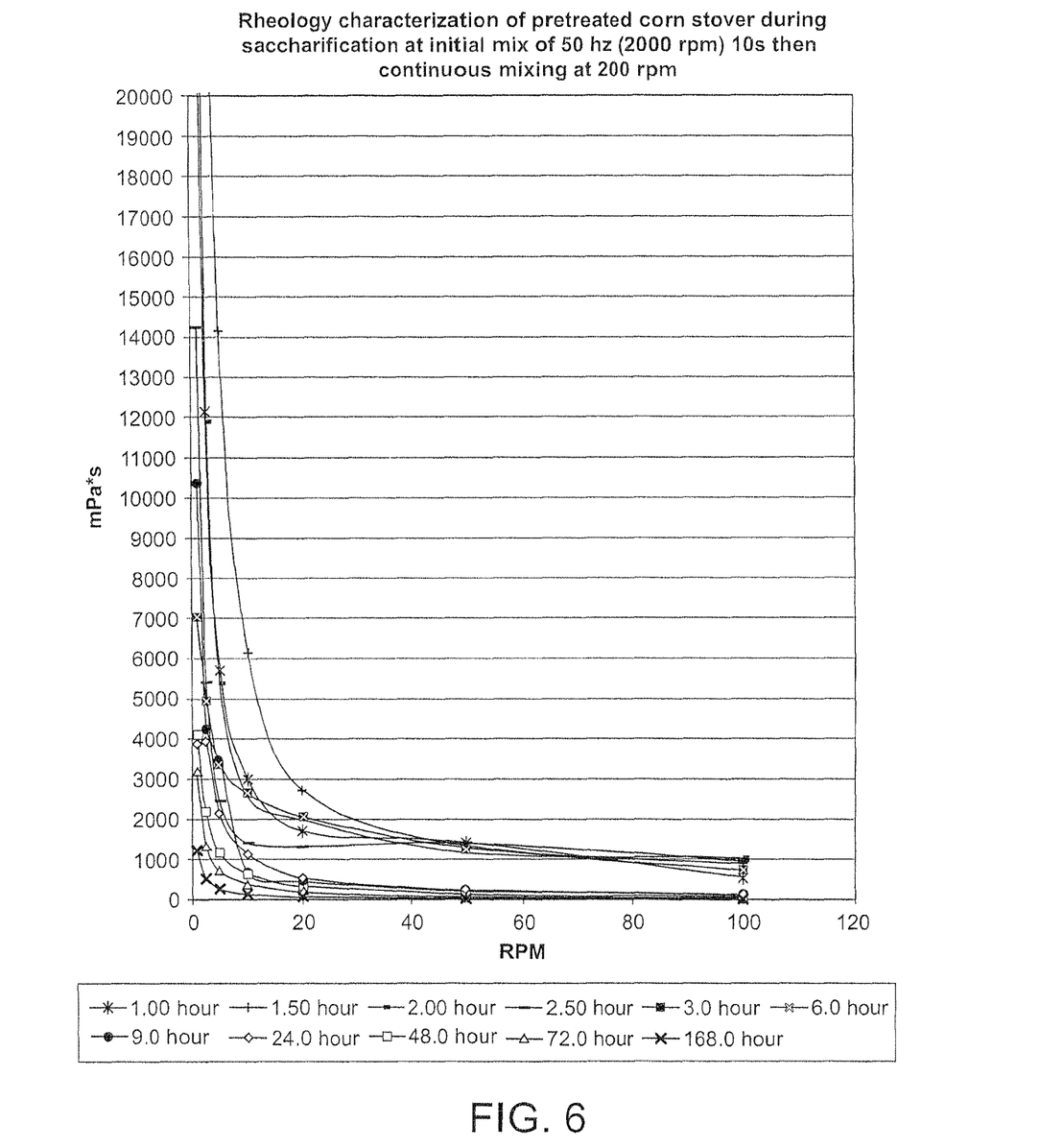
FIG. 6 is a graph further illustrating rheology characterization during saccharification.

FIG. 6 is a graph illustrating the rheology characterization of pretreated corn stover during saccharification at an initial mix of 50 hz (2000 rpm) and 10 seconds, and then continuous mixing at 200 rpm. FIG. 6 shows that the viscosity (mPa*s) of corn stover is reduced by mixing the stover during enzymatic saccharification at rotational speeds of above 20 rpm, and after the initial mix of enzymatic saccharification.

Figure 7:
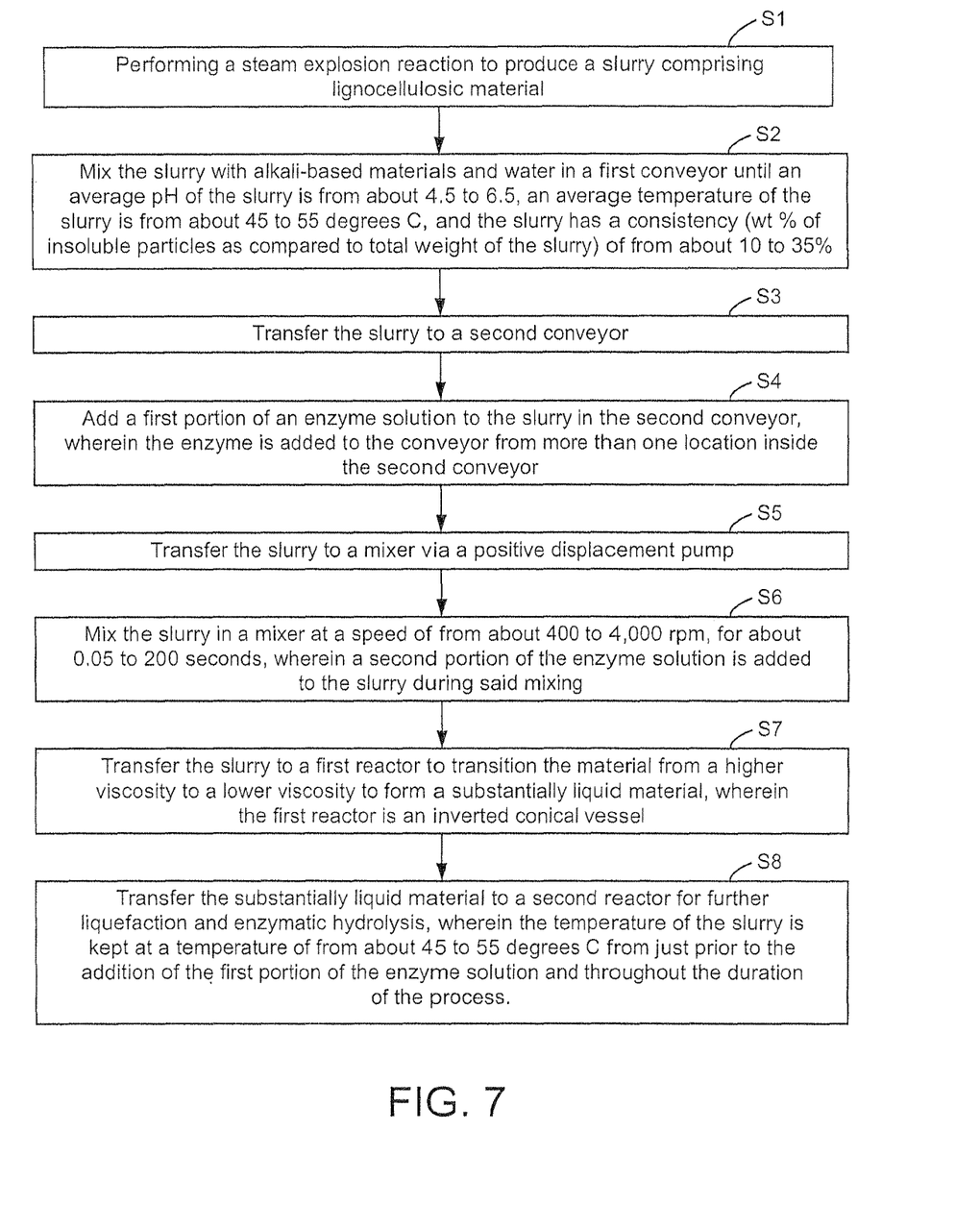
FIG. 7 is a flow chart detailing steps of a certain exemplary embodiment of the invention.

FIG. 7 illustrates an example method for liquefaction according to an aspect of this invention. A slurry comprising lignocellulosic materials is provided. The temperature, pH and consistency of the slurry are altered until they fall into a particular range most suitable for a particular enzyme or enzyme solution. After the desired temperature, pH and consistency are reached, portions of an enzyme solution are added to the slurry, and the slurry is mixed in different stages until its viscosity is lowered such that it becomes a liquid. The slurry undergoes an enzymatic hydrolysis reaction. The enzymatic hydrolysis of the slurry may produce monomeric sugars.

This example method comprises: performing a steam explosion reaction to produce a slurry comprising lignocellulosic material in step S1. Mixing the slurry with alkali-based materials and water in a first conveyor until an average pH of the slurry is from about 4.5 to 6.5, an average temperature of the slurry is from about 45 to 55 degrees C., and the slurry has a consistency (wt % of insoluble particles as compared to total weight of the slurry) of from about 10 to 35% in step S2. Transferring the slurry to a second conveyor in step S3. Adding a first portion of an enzyme solution to the slurry in the second conveyer, wherein the enzyme is added to the conveyer from more than one location inside the second conveyor in step S4. Transferring the slurry to a mixer via a positive displacement pump in step S5. Mixing the slurry in a mixer at a speed of from about 400 to 4,000 rpm, for about 0.05 to 200 seconds, wherein a second portion of the enzyme solution is added to the slurry during said mixing in step S6. Transferring the slurry to a first reactor to transition the material from a higher viscosity to a lower viscosity to create a substantially liquid material, wherein the first reactor is an inverted conical vessel in step S7. Transferring the substantially liquid material to a second reactor for further liquefaction and enzymatic hydrolysis, wherein the temperature of the slurry is kept at a temperature of from about 45 to 55 degrees C. from just prior to the addition of the first portion of the enzyme solution and throughout the duration of the process, in step S8.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A method to treat a lignocellulosic material comprising:
pretreating the lignocellulosic material to produce a slurry including the lignocellulosic material and a liquid;
adding an alkali material to the slurry in a first conveyor, wherein the alkali material increases the average pH of the slurry moving through the first conveyor;
transferring the slurry with the alkali material from the first conveyor to a second conveyor;
adding a first portion of an enzyme solution to the slurry while the slurry is in the second conveyor, entering the second conveyor, or passing through the discharge of the second conveyor;
transferring the slurry with the enzyme solution from the second conveyor slurry to a mixer;
mixing the slurry with a second portion of the enzyme solution, wherein the second portion of the enzyme solution is added to the slurry during the mixing, and
transferring the slurry with the enzyme solution mixed with the first and second portions of the enzyme solution to a first reactor vessel, and
subjecting the slurry in the first reactor vessel to enzymatic hydrolysis, wherein the viscosity of the slurry is reduced in the first reactor vessel.

2. The method of claim 1 further comprising discharging the slurry as a substantially liquid material from the first reactor vessel and transferring the slurry to a second reactor vessel for further enzymatic hydrolysis, wherein the first reactor vessel includes an upper section adjacent an inlet for the slurry, the upper section including a frustoconical outer wall and a cross-sectional area expanding in a downward direction.

3. The method of claim 1 further comprising maintaining the temperature of the slurry in a range of about 45 to 55 degrees C. from the addition of the first portion of the enzyme solution to at least a discharge from the first reactor vessel.

4. The method of claim 1 wherein the first reactor includes an upper inlet receiving the slurry with the enzyme solution, an upper section having an cross-sectional area expanding in a downward direction and the upper section includes an internal rotating mixer with rotating arms extending radially outward from a vertically oriented axial shaft and the arms being successively longer as the cross-sectional area of the upper section increases.

5. The method of claim 1 wherein the slurry with the alkali material in the first conveyor has an average pH in a range of about 4.5 to 6.5, an average temperature in a range of about 45 to 55 degrees Celsius (C), and a consistency in a range of about 10 to 35 wt % wherein the wt % is a ratio of insoluble particles in the slurry and the total weight of the slurry.

6. The method of claim 1 wherein the first portion of the enzyme solution is added to the slurry at a plurality of locations within the second conveyor.

7. The method of claim 1 wherein the mixing step is performed using a mixer vessel having a stirring device rotating at a speed in a range of about 400 to 4,000 revolutions per minute (rpm).

8. The method of claim 1 wherein the slurry remains in the mixing step for a period in a range of about 0.05 to 200 seconds.

9. The method of claim 1 wherein the pretreatment includes a steam explosion process performed on the lignocellulosic material.

10. A method of liquefaction comprising:
pre-treating a lignocellulosic material to produce a slurry comprising the lignocellulosic material and a liquid;
mixing the slurry with an alkali-based material in a first screw conveyor until an average pH of the slurry is in a range of about 4.5 to 6.5, an average temperature of the slurry is in a range of about 45 to 55 degrees C., and the slurry has a consistency in a range of about 10 to 35 wt % wherein the wt % is of insoluble particles as compared to total weight of the slurry;
transferring the slurry to a second screw conveyor;
adding a first portion of an enzyme solution to the slurry in the second screw conveyer, wherein the first portion of the enzyme solution is added to the second conveyer at more than one location along the second screw conveyor;
transferring the slurry to a mixer via a positive displacement pump;
mixing the slurry in the mixer having an agitation device rotating at a speed in a range of about 400 to 4,000 rpm, for a period in a range of about 0.05 to 200 seconds, wherein a second portion of the enzyme solution is added to the slurry during said mixing;
transferring the slurry from the mixing step to a first reactor section to transition the slurry from a higher viscosity to a lower viscosity, wherein the first reactor section includes a frustoconical outer wall, a cross-sectional area expanding in a downward direction and a rotating mixer with arms extending radially from a vertically oriented axial shaft and the arms become successively longer as the diameter of the frustoconical outer wall expands, and
transferring slurry from the first reactor section to a second reactor section for further liquefaction and enzymatic hydrolysis, wherein the temperature of the slurry is kept at a temperature in a range of about 45 to 55 degrees C.

from just prior to the addition of the first portion of the enzyme solution and throughout the duration of the process.

11. The method of claim 10 wherein the first reactor section includes an open bottom and the second reactor section is immediately below the first reactor section, and the second reactor section includes a cylindrical outer wall having an open top connected to the open bottom of the first reactor section, wherein the transferring of the slurry from the first reactor section to the second reactor section includes the slurry moving down through the open bottom of the first reactor section and into the open top of the second reactor section.

12. The method of claim 10 further comprising temporarily retaining the slurry from the second conveyor in a buffer tank and pumping the slurry from a buffer tank by a positive displacement pump to the mixer.

13. The method of claim 10 wherein the mixing in the first screw conveyor cools and increases the pH of the slurry as compared to the conditions of the slurry entering the first screw conveyor.

14. The method of claim 10 wherein the adding of the first portion of the enzyme solution includes adding the first portion of the enzyme solution at a plurality of locations along a longitudinal length of the second screw conveyor.

15. The method of claim 10 wherein the second reactor section includes a plurality of second reactor vessels each receiving the slurry from the first reactor section.

16. The method of claim 10 wherein the pretreatment includes a steam explosion process.

17. A system to liquefy a lignocellulosic material comprising:
a pretreatment reactor receiving the lignocellulosic material saturated with water, treating the saturated material and discharging a slurry comprising the treated saturated material from pretreatment reactor;
a first screw conveyor in fluid communication with a discharge of the pretreatment reactor, the first screw conveyor including a rotating screw, wherein the slurry discharged from the pretreatment reactor passes through the first screw conveyor, and, wherein an alkali-based material is injected through an inlet into the slurry passing through the first screw conveyor;
a second screw conveyor in fluid communication with a discharge of the slurry from the first screw conveyor, wherein the second screw conveyor includes a rotating screw, wherein the slurry from the first screw conveyor passes through the second screw conveyor and an enzyme is injected through a plurality of inlets into the slurry in the second screw conveyer;
a mixer in fluid communication with a discharge of the second screw conveyor, wherein the mixer includes a mixing device rotating at a speed of about 400 to 4,000 rpm, and the mixer retains the slurry from the second screw conveyor for about 0.05 to 200 seconds, and the mixing includes an inlet, wherein the enzyme is added through the inlet to the slurry during mixing, and
a first reactor section, wherein the slurry transitions from a high viscosity to a low viscosity to create a substantially liquid slurry in the first reactor section, wherein the first reactor section includes a frustoconical outer wall, a cross-sectional area expanding in a downward direction, and a mixing device with rotating radial arms extending from a vertically oriented axial shaft wherein the rotating radial arms are progressively longer as the cross-sectional area expands.

18. The system of claim 17 wherein:
the first reactor section includes an open bottom, and
the system further comprises a second reactor section immediately below the first reactor section and the second reactor section includes a cylindrical wall having an open top connected to the open bottom of the first reactor section.

19. The system of claim 17 further comprising a buffer tank temporarily retaining the slurry from the second screw conveyor and discharging the slurry to a positive displacement pump fluidly coupled to the mixer.

20. The system of claims 17 wherein the inlets for enzyme injection are equally spaced at a plurality of locations along a length of a screw of the second screw conveyor.

21. The system of claims 17 wherein the second reactor section includes a plurality of second reactors each receiving the slurry from the first reactor section.

22. The system of claim 17 wherein the pretreatment reactor receives the lignocellulosic material saturated with water, subjects the material to a rapid pressure release to cause a steam explosion reaction and discharges the slurry comprising the lignocellulosic material after the steam explosion reaction.

* * * * *